(12) United States Patent
Davelaar et al.

(10) Patent No.: US 7,211,260 B1
(45) Date of Patent: May 1, 2007

(54) INFECTIOUS BURSITIS VACCINE

(75) Inventors: Frans Gerrit Davelaar, Putten (NL); Bernarda Johanna Pitstra, Weesp (NL); Nico Van Wiltenburg, Abcoude (NL)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 09/355,374

(22) PCT Filed: Jan. 29, 1998

(86) PCT No.: PCT/EP98/00461

§ 371 (c)(1),
(2), (4) Date: Mar. 7, 2000

(87) PCT Pub. No.: WO98/33522

PCT Pub. Date: Aug. 6, 1998

(30) Foreign Application Priority Data

Feb. 3, 1997 (EP) ........................... 9720020098

(51) Int. Cl.
*A61K 39/215* (2006.01)

(52) U.S. Cl. .................... 424/204.1; 435/236
(58) Field of Classification Search ............ 424/184.1, 424/204.1, 215.1; 435/236
See application file for complete search history.

(56) References Cited

U.S. PATENT DOCUMENTS 4,530,831 A * 7/1985 Lütticken et al. .......... 424/89
4,824,668 A    4/1989 Melchior, Jr. et al.
5,192,539 A    3/1993 Van Der Marel et al.
5,804,195 A * 9/1998 Gutter ................... 424/202.1

FOREIGN PATENT DOCUMENTS

| EP | 0 600 723 A3 | 6/1994 |
| EP | 0 861 665 A1 | 9/1998 |
| WO | WO 91/05569 | 5/1991 |
| WO | WO 98/33522 | 8/1998 |

OTHER PUBLICATIONS

Murphy, F. A., 1996, "Virus Taxonomy", in *Fields Virology, Third Edition*, eds. Fields, B. N., et al., Lippincott–Raven Publishers, Philadelphia, p. 19.*

Kouwenhoven et al., Poultry Health Institute, Proceedings 19th World's Poultry Congress, Amsterdam Sep. 19–24, 1992, vol 1, pp 465–468, Control of Very Virulent Infectious Bursal Disease (Gumboro Disease) in the Netherlands with So Called "Hot" Vaccines.

Lasher et al., World's Poultry Science Journal, vol 50, Jul. 1994, pp 133–166, Infectious Bursal Disease.

Lukert et al., Diseases of Poultry, Ninth Edition, Iowa State University Press 1991, pp 648–663, Infectious Bursal Disease.

* cited by examiner

*Primary Examiner*—Jeffrey S. Parkin

(57) ABSTRACT

The present invention is concerned with isolated infectious bursitis (or bursal) disease virus(es) and a vaccine containing said virus(es) which is capable of protecting poultry against disease caused by infectious bursitis virus, characterized in that the vaccine virus(es) has/have the combined properties of, upon administration to a chicken, causing a reduction in the bursal size, expressed as bursa/body weight ratio, of less than 55%, and the capability to protect poultry having an ELISA antibody titer of at least about 500.

11 Claims, No Drawings

INFECTIOUS BURSITIS VACCINE

The present invention is concerned with a vaccine which is capable of protecting poultry against Infectious Bursitis infections, and with novel viruses useful for preparing such vaccines.

Infectious Bursitis is an infective disease which can afflict poultry and which is caused by the Infectious Bursal Disease Virus (IBDV). The agent of Infectious Bursitis belongs to the family Birnaviridae, genus Birnavirus and affects primarily the Bursa of Fabricius. This causes an atrophy of the Bursa. Infection with the virulent viruses found in the field generally causes reduction of the bursa weight to approximately one-third of the normal weight. This is normally expressed as the bursa/body weight ratio (BBR). The disease gives degeneration and necrosis of the B lymphocyte population of the bursa. This may result in immunosuppression. The degree of atrophy (and subsequent degeneration) of the bursa depends on the virulence of the strain involved.

Serologically IBDV can be distinguished into two different types: type 1 is found in chickens, whereas type 2 is found in turkeys.

Prevention of Infectious Bursitis is based on vaccination. The vaccine strains currently in use are divided into highly virulent (=intermediate plus; examples: Bursine Plus, Bursine 3), intermediate virulent (e.g. Bursine 2, D78, LZ228TC) and highly attenuated mild (=avirulent; e.g. Bursine 1) strains.

The problem faced by poultry farmers is that in a regimen in which poulty flocks are regularly vaccinated, the newly hatched chicks are born with a high maternal antibody titre. It is known that maternal antibody titres interfer with the vaccine virus. Highly virulent, intermediate and avirulent strains break through maternal virus-neutralizing antibody levels of 1:500, 1:250 or less than 1:100, respectively ("Diseases of Poultry", ninth edition, ed: Calnek et al.; Iowa State University Press, 1991, p. 659). Using the ELISA system to monitor maternal antibodies, comparable results are obtained. The virulent (intermediate plus) vaccines break through IDDEX-ELISA titers of about 500. Intermediate and mild strains are found to break through much lower titers to induce a seroresponse.

The virulence of strains is monitored by the effect on the bursa weight (BBR) as described earlier, or by the microscopical changes. The following table (TABLE 1) shows the level of virulence of intermediate plus vaccines (Poulvac Bursa Plus, Delvax LZ228E) and of virulent field virus (isolate D6948E) on the Bursa weight (expressed as percentage BBR as compared to normal).

TABLE 1

| strain/vaccine | BBR 3 w. after inoculation (% of controls) |
| --- | --- |
| Poulvac Bursa Plus | 27 |
| Delvax LZ228E | 39 |
| D6948E 10a89 | 27 |
| D6948E 10a89 | 39 |
| mean | 33 |

The comparison shows that the intermediate plus vaccines affect the bursa weight as much as the virulent field virus. As a consequence, practitioners who wish to vaccinate young chickens with high maternal antibody titers have to accept the negative consequences of the more "hot" strains (such as severe tracheal lesions and a high death rate) as well. Therefore, farmers lose chicks with >1:500 antibody titre when using intermediate vaccines because it does not break through this titre, and when using a virulent vaccine, farms lose chicks because of the effect of the virus.

Hence, there is a need for a vaccine which is less virulent and capable of breaking through high maternal antibody titers at the same time.

Surprisingly, IBDV with this set of characteristics has been found. Thus, according to the present invention, there is provided a vaccine which is capable of protecting poultry against Infectious Bursitis infections, characterized in that it contains an Infectious Bursal Disease virus which has the combined properties of an intermediate virulence and the capability to protect poultry with an ELISA antibody titer of at least about 500.

A particular example of this new class of viruses has been isolated. The new IBDV strain is internally indicated as strain 9793, a sample of which has been deposited at the Collection Nationale de Cultures de Microorganismes of Institut Pasteur at Paris (France) under No. 1-1810 on Jan. 22, 1997. The deposited material 1-1810 is in the form of the master seed virus.

The vaccine virus is prepared from Seed virus by one or more passages on a suitable medium. Preferably, all vaccine virus is derived from a single stock virus pool—the Master Seed virus. Optionally a Working Seed Virus pool is prepared from this Master. Seed by one or more passages, and the actual vaccine virus is prepared from this Working Seed by one or more passages as well. The vaccine normally contains a stabiliser, such as inisitol or manitol, which is used in the preparation process. If required a diluent for the vaccine can be any physiological solution.

Suitable media for passaging during these respective propagation steps from Master Seed to vaccine virus are for example Specific Pathogen Free (SPF) eggs, Specific Antibody Negative (SAN) eggs, primary chicken cells or an avian cell line.

The vaccine according to the present invention preferably contains live viruses of the new IBDV class described above. The effective dose per chicken can vary between about $10^2$ and about $10^6$ $EID_{50}$, preferably between about $10^3$ and $10^5$ $EID_{50}$. The vaccine can be administered safely to one-day-old chicken and in ovo.

The vaccine according to the present invention based on live IBDV preferably is shipped in freeze-dried form and dissolved in water prior to use.

The vaccine according to the present invention preferably is administered by the enteral route, e.g. orally (in the drinking water or individually by pipette), oculonasally or by spray.

The IBDV strain 9793 is characterised by the ability to induce antibody in birds with a maternal antibody level of $\geq 500$ (measured by IDDEX ELISA) and because it is much less damaging to the bursa than hot vaccines. Induction of antibody in birds with a maternal antibody level of $\geq 500$ is normally only possible with so called "hot" vaccines and/or virulent field strains. These hot vaccines and field strains will badly damage the Bursa of Fabricius causing a depletion of B lymphocytes. IBDV strain 9793 is much less damaging to the bursa as measured by the size of the bursa after infection.

Thus, in further aspects of the invention there is provided a vaccine comprising a virus of the strain 9793, having the general or specific characteristics of deposit No. 1-1810, or a vaccine comprising a virus derived or developed from strain 9793, i.e. derived or developed from either the actual deposit or obtaining the virus from nature. There is also provided IBD virus having the general or specific characteristics of deposit No. 1-1810, or a vaccine comprising a virus derived or developed from strain 9793, i.e. derived or developed from either the actual deposit or obtaining the virus from nature.

The invention is illustrated, but not limited, by the following examples.

EXAMPLE 1

Preparation of the Master Seed Virus

Two vials of the mother material of strain 9793 were resuspended in 2.0 ml of distilled water. This virus suspension was diluted 1/10 by transferring 1 ml thereof into 9 ml of saline. After mixing this was diluted 1/30 by transferring 2 ml into 58 ml of saline to give a suspension containing approximately 500 $EID_{50}$ per 0.1 ml. Four hundred embryos of SAN eggs were each inoculated with 0.1 ml of the above virus suspension via the yolk sack route using a 1 ml syringe fitted with a 23 G×1" needle. The eggs were incubated at 37° C. and candled after 24 hours. Forty-nine embryos were dead and discarded. Forty-eight and seventy-two hours after inoculation the dead embryos (340 eggs total) were removed from the eggs and decapitated. They were pooled into groups of approximately 50 embryos. Each group was homogenized separately using an Ystral blender fitted with a small autoclavable shaft. Each homogenate was poured through two layers of gauze over a beaker and each filtrate was transferred to a separate Duran bottle. A volume of stabiliser, containing inositol and manitol, equivalent to approximately one third of the volume of the filtrate was added to each. Samples of 2 or 3 ml were taken from each bottle for titration or sterility testing respectively. The bottles and the samples were frozen and stored at −70° C. until further processing. Sterile bottles were thawed, pooled and mixed well using a magnetic stirrer. A total volume of 496 ml of master seed suspension was filled into vials, 0.5 ml per vial, placed in the Edwards Lyomaster 4000 and freeze-dried. The vials were closed under vacuum with rubber stoppers and sealed with aluminium capsules.

EXAMPLE 2

Preparation of the Working Seed

One vial of the Master Seed Virus of strain 9793 was resuspended in 1.0 ml of distilled water. This was diluted 1/10 by transferring 0.2 ml thereof in 1.8 ml of saline. After mixing this was diluted 1/200 by transferring 1 ml in 199 ml of saline to give a suspension containing approximately $10^4$ $EID_{50}$ per 0.1 ml. Six hundred and fifty embryos of SAN eggs were each inoculated with 0.1 ml of the above virus suspension via the yolk sack route using a 1 ml syringe fitted with a 23 G×1" needle. The eggs were incubated at 37° C. and candled after 24 and 48 hours. Twelve embryos were dead after 24 hours and eleven after 48 hours. These were all discarded. Seventy-two hours after inoculation the embryos were removed from the remaining eggs and decapitated. They were pooled into ten groups of approximately 60 embryos. Each group was homogenized separately using an Ystral blender fitted with a small autocavable shaft. Each homogenate was poured through two layers of gauze over a beaker and each filtrate was transferred to a separate Duran bottle. A volume of stabiliser, containing inositol and manitol, equivalent to approximately one third of the volume of the filtrate was added to each. The final volume of each was between 50 and 60 ml. 1 ml was removed from each Duran bottle and pooled. After mixing this was dispensed in 1 ml aliquots into Nunc Cryotubes and these were stored at −70° C. for later titration. A further 1 ml aliquot was removed from each Duran bottle and plated individually onto 5% Blood agar plates to check for sterility. The Duran bottles were all stored at −70° C. until required. There was no growth on any of the plates after 14 days, therefore all ten aliquots were included in the working seed.

Freeze Drying and Testing of the Working Seed

Each of the Working Seed aliquots were thawed, pooled and mixed well on a magnetic stirrer using a follower. Four hundred and twenty vials were each filled with 1 ml of virus suspension. The vials were placed into the Modulyo freeze drier. Freeze drying was carried out for fourteen hours before the vials were sealed and removed from the Clean Room. Crimp tops were applied to each vial and they were all tested for vacuum using an Edwards spark tester.

Preparation of the Vaccine

The vaccine material itself was prepared according to the method as outlined above from the Working Seed. A stabiliser was added (inositol, manitol) to the vaccine material.

EXAMPLE 3

Safety of the Vaccine

Safety of the vaccine prepared according to EXAMPLE 1 was tested after vaccination of one-day old chickens according to two methods explained below.

Bursa/body Weight Ratio

The bursa size is expressed as the bursa/body weight ratio (BBR) according to the following formula:

$$BBR = \frac{\text{bursa weight (g)} \times 1000}{\text{body weight (g)}}$$

Lesion Score of Bursa

The lesions seen by microscopical examination are judged as follows:

After weighing, the removed bursae were fied in 4% formalin for microscopical examination at the PHC, Doorn, The Netherlands. The results were scored as summarized in TABLE 2.

TABLE 2

| SCORE | OBSERVATIONS |
|---|---|
| 0 | No damage. |
| 1 | Some necrosis/lymphodepletion in isolated follicles. |
| 2 | Moderate generalized lymphodepletion or severe lymphodepletion in isolated follicles. Some fibrosis, some epithelial proliferation. |
| 3 | Over 50% of follicles with severe lymphodepletion. Fibrosis and epithelial proliferation. Some follicles have been replaced by cavities, initially filled with necrotic tissue (approx. 6 days post-infection), later on (after clearance of the necrotic tissue) lined with epithelium. |
| 4 | All follicles display severe lymphodepletion; only in their cortex lymphocytes may be discernible. Marked fibrosis and epithelial proliferation. Several follicles have been replaced by the afore-mentioned cavities. |
| 5 | Total loss of follicular architecture. Severe fibrosis and epithelial proliferation. The afore-mentioned cavities are scattered throughout the bursal tissue. |

Groups of 30 birds each were vaccinated with the 9793 vaccine by spray, except for the controls. Three weeks after vaccination half of the birds of each group were killed and the BBR was determined. The remaining half of the birds of each group were challenged at 3 weeks after vaccination. This challenge was carried out using a highly virulent field strain (D6948E, obtained from the Animal Health Institute at Deventer, The Netherlands). 10–12 days after challenge these birds were sacrificed as well and the BBR was determined. From a selected number of groups both prior to and after challenge the bursa were examined microscopically and the lesion score was determined.

Results

BBR

The results of the BBR determinations are summarized in TABLE 3. These results show that the % BBR compared to the controls after vaccination as a mean is about 60. Hence, it can be concluded that the damage to the bursa by the vaccine virus is very moderate. Furthermore, it is clear that the effect of the challenge virus to the bursa of vaccinated birds is absent, whereas in the control birds a considerable damage to the bursa is prominent. These latter data from the control birds in fact confirm the data earlier presented for field viruses and virulent vaccine strains.

TABLE 3

| trial/ | % BBR compared to the controls | |
|---|---|---|
| group | 3 w. after vaccination | 10–12 days post-challenge |
| 1a | 46 | 47 |
| 1b | 68 | 56 |
| 1c* | 100 | 37 |
| 2a | 45 | 55 |
| 2b | 46 | 59 |
| 2c* | 100 | 38 |
| 3a | 51 | 62 |
| 3b | 93 | 40 |
| 3c* | 100 | 27 |
| mean vaccinated | 58.7 | 52 |
| mean control | 100 | 34.0 |

*non-vaccinated controls.

Microscopical Examination

The microscopically visible damage to the bursa is summarized in TABLE 4. The lesion score after vaccination is very low and at an acceptable level for a vaccine, whereas a very high score is found in unvaccinated birds after challenge. The bursa of vaccinated birds again showed to be unaffected by the challenge virus.

TABLE 4

| trial/ | microscopical score | |
|---|---|---|
| group | 3 w. after vaccination | 10 days post-challenge |
| 3a | 1.8 | 1.2 |
| 3b | 1.5 | 1.2 |
| 3c* | 0.6 | 4.2 |

*non-vaccinated controls.

EXAMPLE 4

Seroresponse After Vaccination

These studies were carried out with the birds used for EXAMPLE 3. Blood samples of the birds were taken at approximately 5 or 6 days of age. Individual titers 2–5 days later were calculated according to the formula of Kouwenhoven (B. Kouwenhoven and J. van den Bosch; in: Proceedings of 19th World's Poultry Congress, 1992, p. 465–468). Birds were divided then over different titer groups and vaccinated. During 3 or 4 weeks, blood samples were taken to examine seroconversion.

Results

The results of these studies are summarized in TABLE 5. These data confirm the high efficacy of the vaccine according to the present invention. High levels of maternal antibodies do not interfere with the vaccination. Kouwenhoven (supra) gives ELISA titers of about 500 that intermediate plus strains are able to break through. The vaccine according to the present invention easily breaks through higher levels of maternal antibodies to induce seroconversion.

TABLE 5

| trial | calculated titer | vacc. dose | mean antibody titer to IBD at days p.v. | | | |
|---|---|---|---|---|---|---|
| group | at day of vacc. | ($^{10}$log EID$_{50}$) | 7 | 14 | 21 | 28 |
| 1a | 122 | 3.4 | 2 | 1061 | 1560 | ND |
| 1b | 939 | 3.4 | 18 | 676 | 1088 | ND |
| 1c* | 142 | — | 2 | 80 | 134 | ND |
| 2a | 668 | 3.7 | ND | 3 | 410 | 1434 |
| 2b | 649 | 3.7 | ND | 83 | 946 | 1808 |
| 2c* | 1054 | — | ND | 85 | 3 | 31 |
| 3a | 256 | 3.7 | ND | 760 | 2167 | ND |
| 3b | 2235 | 3.7 | ND | 202 | 737 | ND |
| 3c* | 1089 | — | ND | 42 | 55 | ND |

*non-vaccinated controls; "ND" means not determined.

EXAMPLE 5

Bloodsamples were taken from one-day old chicks in order to calculated the vaccination day using the Kouwenhoven formula previously mentioned.

Two trials were set up, A and B, to determine effects of strain 9793 on mortality. For trial A bloodsamples were taken at one day old, at 14 (day of vaccination with strain 9793), 21, 28 and 35 days. Bloodsamples were taken at one day old, and at I I (day of vaccination with strain 9793), 21, 28 and 35 days of age for trial B.

In both experiments one group was vaccinated for IBD and the other group acted as controls. Each group consisted of 1,500 chicks.

All chicks were vaccinated against Newcastle disease (ND), and Infectious Bronchitis (IB) at day of vaccination. Vaccines used were Poulvac NDW (Newcastle disease vaccine) and Poulvac IB Primer (Infectious Bronchitis vaccine containing strains H120 and D274). Vaccination was done by coarse spray. Serology was done by the HI test for ND and IB and by the IDEXX ELISA for IBD. Finally mortality was monitored. Data on serology are given in the Tables 6A and 6B (trial 97-62 A and 97-62 B).

Mortality was as follows:

Trial A:
  IBD vaccinated (group 1)=7%
  unvacc. controls (group 2)=6.4%

Trial B:
  IBD vaccinated (group 2)=2.8%
  unvacc. controls (group 1)=5.1%

Trial B shows that IBD 9793 breaks through maternal antibodies >500. In trial A maternal antibodies were below 500 on the day of vaccination. Serology data for IB and ND do not show any immunosuppression by IBD 9793 on the humoral antibody response to IB or ND. Mortality data also demonstrate that the vaccine is safe.

TABLE 6A

Mean HI antibody titres to NDV, IBV M41 and IBV D 274 and mean ELISA antibody titres to IBDV.

| age | no. sera | mean HI antibody titres | | | mean ELISA antibody titres |
| --- | --- | --- | --- | --- | --- |
| | | ND | IB M 41 | IB D274 | IBD | on day

| | | | | | |
| --- | --- | --- | --- | --- | --- |
| group 1 | 24 | 4.2 | 7.7 | 7.3 | 3538 |
| group 2 | 24 | 4.2 | 7.5 | 7.2 | 4208 |

14 days. Day of vaccination with stain 9793 (group 1)

| group 1 | 24 | 4.2 | 6.3 | 5.7 | 224 |
| --- | --- | --- | --- | --- | --- |
| group 2 | 24 | 2.0 | 5.3 | 5.4 | 354 |

21 days. 1 week p.v.

| group 1 | 48 | 3.2 | 4.1 | 4.2 | 55 |
| --- | --- | --- | --- | --- | --- |
| group 2 | 48 | 3.2 | 3.8 | 5.0 | 30 |

28 days. 2 weeks p.v.

| group 1 | 48 | 3.4 | 5.0 | 3.8 | 399[1] |
| --- | --- | --- | --- | --- | --- |
| group 2 | 48 | 3.6 | 5.4 | 4.0 | 5 |

35 days. 3 weeks p.v.

| group 1 | 48 | 2.7 | 4.0 | 4.3 | 1708[1] |
| --- | --- | --- | --- | --- | --- |
| group 2 | 48 | 3.2 | 4.2 | 4.6 | 4 |

[1]statistically significant difference ($P \leq 0.05$) between groups using one-way ANOVA with factor group.

TABLE 6B

Mean antibody titres against ND, IB M41, IB D274 and IBD

| age | no. sera taken | mean HI antibody titres | | | mean ELISA antibody titres |
| --- | --- | --- | --- | --- | --- |
| | | ND | IB M 41 | IB D274 | IBD | on day

| group 1 | 24 | 5.2 | 8.1 | 8.3 | 3113 |
| --- | --- | --- | --- | --- | --- |
| group 2 | 24 | 4.9 | 8.5 | 8.7 | 3386 |

11 days. Day of vaccination with 9793 (group 2)

| group 1 | 24 | 3.4 | 7.2 | 7.4 | 623 |
| --- | --- | --- | --- | --- | --- |
| group 2 | 24 | 2.7 | 6.4 | 6.9 | 743 |

21 days. 10 days p.v.

| group 1 | 48 | 3.1 | 5.4 | 5.7 | 25[1] |
| --- | --- | --- | --- | --- | --- |
| group 2 | 48 | 3.8 | 5.2 | 5.8 | 157 |

TABLE 6B-continued

Mean antibody titres against ND, IB M41, IB D274 and IBD

| age | no. sera taken | mean HI antibody titres | | | mean ELISA antibody titres |
| --- | --- | --- | --- | --- | --- |
| | | ND | IB M 41 | IB D274 | IBD |

28 days. 17 days p.v.

| group 1 | 48 | 3.3 | 4.2 | 6.6 | 35[1] |
| --- | --- | --- | --- | --- | --- |
| group 2 | 48 | 3.2 | 4.1 | 6.4 | 773 |

35 days. 3 weeks p.v.

| group 1 | 48 | 3.6 | 3.9 | 5.4 | 89[1] |
| --- | --- | --- | --- | --- | --- |
| group 2 | 48 | 4.0 | 4.0 | 5.6 | 1634 |

[1]statistically significant difference ($P \leq 0.05$) between groups using one-way ANOVA with factor group.

What is claimed is:

1. An isolated and purified infectious bursitis virus strain having the CNCM accession number I-1810.

2. An isolated and purified infectious bursal disease virus strain designated 9793.

3. An isolated and purified infectious bursal disease virus strain designated 9793, a sample of which is deposited at CNCM under accession number I-1810.

4. An infectious bursitis vaccine virus prepared by passaging the virus of claim 1, or 2.

5. A vaccine composition that is capable of protecting poultry against infectious bursitis infections comprising an isolated and purified infectious bursitis virus having the CNCM accession number I-1810.

6. A vaccine composition comprising an isolated and purified infectious bursitis virus strain designated 9793.

7. A vaccine composition comprising an isolated and purified infectious bursitis virus strain designated 9793, a sample of which is deposited at CNCM under accession number I-1810.

8. A vaccine composition that is capable of protecting poultry against infectious bursitis infections comprising a vaccine virus according to claim 4.

9. A vaccine composition according to claim 8 comprising live viruses.

10. A vaccine composition according to claim 8 comprising an effective dose per chicken of about $10^2$ to $10^6$ $EID_{50}$.

11. A vaccine composition according to claim 8 comprising an effective dose per chicken of about $10^3$ to $10^5$ $EID_{50}$.

* * * * *